| United States Patent [19] | [11] | 4,172,765 |
|---|---|---|
| Keyes | [45] | Oct. 30, 1979 |

[54] METHOD FOR THE QUANTITATIVE DETERMINATION OF ALPHA-AMYLASE

[75] Inventor: Melvin H. Keyes, Sylvania, Ohio

[73] Assignee: Technicon Instruments Corporation, Tarrytown, N.Y.

[21] Appl. No.: 833,318

[22] Filed: Sep. 14, 1977

[51] Int. Cl.² ............................................. G01N 31/14
[52] U.S. Cl. ..................... 435/14; 204/1 T; 435/817; 435/22; 435/27; 435/28
[58] Field of Search ................ 195/103.5 S, 103.5 C, 195/103.5 R, 4, 7, 11

[56] References Cited

U.S. PATENT DOCUMENTS 4,000,042  12/1976  Adams ........................... 195/103.5 S

OTHER PUBLICATIONS

Wilson et al., Clinical Chemistry, vol. 21, No. 7, pp. 947-948 (item 36), 1975.
Ceska et al., Clinical Chim. Acta., vol. 26, pp. 437-444 (1969).

*Primary Examiner*—Lionel M. Shapiro
*Attorney, Agent, or Firm*—S. P. Tedesco

[57] ABSTRACT

This invention relates to a method and apparatus for rapid quantitative determination of $\alpha$-amylase in aqueous samples such as blood serum, etc. The method comprises a flow-through of the sample through various immobilized reagents contained in sequential stages. A scavenger stage initially removes glucose originally present in the sample and comprises immobilized glucose oxidase and catalase. The glucose-free sample flows through an immobilized starch stage substrate preferably containing a high percentage of amylose to quantitatively react with the $\alpha$-amylase in the sample and produce oligosaccharides. The sample with the oligosaccharides flows through a glucose-generating stage containing immobilized glucoamylase which converts the oligosaccharides to glucose. The glucose-containing sample enters a detection stage wherein the glucose is converted to $H_2O_2$ by flowing through immobilized glucose oxidase, and the $H_2O_2$ produced is quantitatively detected in detection means such as a polarographic cell. The immobilized reagents are preferably contained in an apparatus which comprises at least one column in combination with the detection means and a readout means.

41 Claims, 2 Drawing Figures

METHOD FOR THE QUANTITATIVE DETERMINATION OF ALPHA-AMYLASE

BACKGROUND OF THE INVENTION

This invention relates to a method and apparatus for the rapid quantitative determination of α-amylase in any fluid which contains α-amylase, particularly in biologic fluids such as blood serum and urine, or any other fluid containing α-amylase and glucose.

Serum amylase is generally regarded as the single most important practical diagnostic test in cases of acute pancreatitis. Procedures for the rapid measurement of α-amylase activity in blood serum have been proposed, and would be desirable wherein a short time is available or required for obtaining the value of the measurement in emergency situations.

Various rapid procedures are disclosed in the patent art for use in determining and monitoring various components in serum solutions, particularly for glucose, urea, etc., e.g. U.S. Pat. Nos. 3,367,849; 3,421,982; 3,512,517; 3,591,480; 3,838,011; 3,926,734; 3,947,328; and others.

With respect to the determination of α-amylase in serum or other body fluids, the following is a list of presently known literature references on the matter:
1. Caraway, W. T., "A Stable Starch Substrate for the Determination of Amylase in Serum and other Body Fluids." Amer. J. Clin. Pathol. 32, 97 (1959).
2. Somogyi, M., "Micro Methods for the Estimation of Blood Diastase." J. Biol. Chem. 125, 399 (1938).
3. Peralta, O., and Reinhold, J. G., "Rapid Estimation of Amylase Activity of Serum by Turbidimetry." Clin. Chem. 1, 157 (1955).
4. Sax, S. M., Bridgewater, A. B., Moore, J. J., "Determination of Serum and Urine Amylase with Use of Procion Brilliant Red M-2BS Amylopectin." Clin. Chem. 17, 311 (1971).
5. Chung, K. Y., Sinha, R. M., and Trew, J. A., "Comparison of Two Methods for Determining Amylase Activity in Serum and Urine." Clin. Chem. 17, 89 (1971).
6. Ceska, M., Birath, K., and Brown, B., "A New and Rapid Method for the Clinical Determination of α-Amylase Activities in Human Serum and Urine. Optimal Conditions." Clin. Chem. ACTA, 26, 437 (1969).
7. Henry, R. J., and Chiamori, N., "Study of the Saccharogenic Method for the Determination of Serum and Urine Amylase." Clin. Chem. 6, 434 (1960).
8. Shipe, J. R., and Savory, J., "Kinetic Nephelometric Procedure For Measurement of Amylase Activity in Serum." Clin. Chem. 18, 1323 (1972).
9. Zinterhofer, L., Wardlaw, S., Jatlow, P., and Seligson, D., "Nephelometric Determination of Pancreatic Enzymes. I. Amylase", Clin. Chem. Acta, 43, 5 (1973).
10. Smeaton, J. R. and Marquart, W. F., "A Reaction Rate Nephelometer for Amylase/Lipase Determinations." Clin. Chem. 20, 896 (1974) Abstract.
11. Smith, B., and Roe, J. H., "A Photometric Method for the Determination of α-Amylase in Blood and Urine with Use of Starch-Iodine Color", J.Biol. Chem. 179, 53 (1949).
12. J. John Marshall et al, "A New Serum α-Amylase Assay of High Sensitivity", Clin. Chem. Acta, 76, 277, (1977).

Most of the methods commercially used for the measurement of alpha-amylase activity use a starch substrate and either measure reducing reaction products which are sugars, or measure the amount of starch hydrolyzed as the reaction progresses. The measurement of the starch substrate is accomplished both chemically and physically by iodometric, turbidimetric, viscosimetric, and dye-complexing methods.

An instrument presently available for measuring the α-amylase activity uses a kinetic, turbidimetric method for the determination of α-amylase activity and uses an insoluble amylopectin substrate with activity determined by the rate of decrease in turbidity.

Although the above procedures have been found satisfactory, it has been a desideratum of persons in the medical field conducting tests for α-amylase in various solutions to have for use a procedure which, among other things, is rapid in its quantitative determination of the α-amylase content, and has ease of operation.

OBJECTS OF THE INVENTION

It is an object of this invention to provide an improved quantitative detecting method and apparatus which possesses high specificity and sensitivity for α-amylase in fluids.

Another object of this invention is to provide a rapid method and apparatus for the quantitative determination of α-amylase, contained in a test sample, comprising immobilized reagents.

A further object of this invention is to provide a method and apparatus for the quantitative determination of α-amylase which includes a scavenger stage comprising immobilized reagents for removing glucose initially present in the sample to avoid erroneous results.

An additional object of this invention is to provide a rapid method and apparatus for the quantitative detection of the α-amylase in a test sample comprising the use of an immobilized starch reagent for quantitatively reacting with the α-amylase in a sample to produce oligosaccharides, which are sequentially converted to glucose. The glucose is converted to a compound which can be quantitatively detected with detection means.

Another object of this invention is to provide an apparatus or instrument for the rapid detection of α-amylase in a test sample comprising a series of sequential stages comprising immobilized reagents wherein a flow-through of the test sample results in a quantitative readout of the amount of α-amylase in the test sample.

SUMMARY OF THE INVENTION

These and other objects are accomplished by a method and apparatus for quantitatively determining the alpha-amylase content of a test sample comprising the removal from the test sample glucose which may initially be present in order to avoid erroneous results. The glucose is removed in a scavenger stage wherein the buffered sample flows through immobilized glucose oxidase and catalase which convert the glucose to gluconic acid, water, and oxygen. The glucose free sample is then passed through a substrate stage comprising a suitable immobilized starch reagent which reacts quantitatively with the alpha-amylase contained in the sample to produce oligosaccharides. The oligosaccharides in the sample are passed to a glucose-generating stage comprising an immobilized reagent, i.e. glucoamylase which converts the oligosaccharides to glucose. The sample containing the glucose passes to a detection stage wherein the glucose contacts an immobilized glucose oxidase reagent forming gluconic acid and $H_2O_2$.

The H₂O₂ is detected in detection means such as an amperometric sensor cell or spectrophotometer connected to suitable readout means.

A feature of this invention is that only a small amount of the sample solution containing the alpha-amylase need be used for passage through the various stages of the method. This is so because of the unique arrangement of the reagents with components of the sample, i.e. the reagents are immobilized and the sample flows sequentially through a column or columns containing the immobilized reagents. With this procedure, response is obtained relating the mg% of alpha-amylase to the signal from the detection cell.

DETAILED DESCRIPTION OF THE INVENTION

Figure 1:
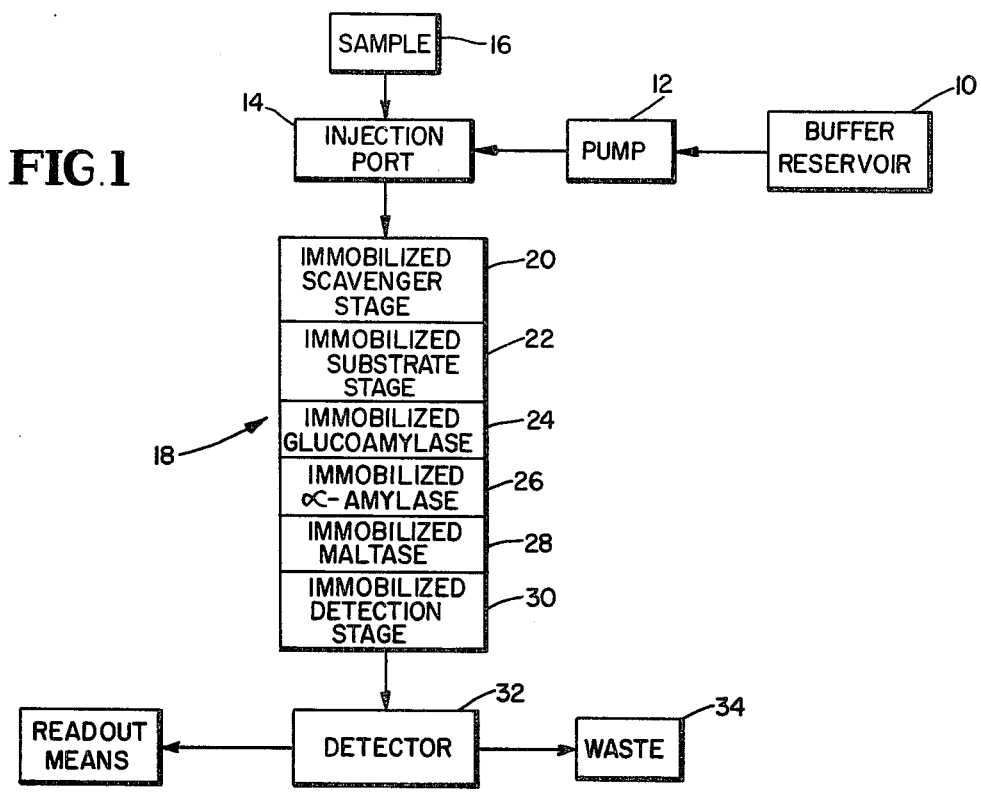

The method of the invention for the detection of α-amylase in a sample comprises a unique and novel flow-through combination of immobilized enzymes, immobilized starch substrates, and scavenger systems with hydrogen peroxide detection means to quantitatively determine the amount of α-amylase present in a sample. All of the component elements of the combined flow-through system cooperate in acting upon selected ingredients of the sample being tested to ultimately give the desired result.

Generally, the method for the detection of the α-amylase in a sample comprises the injection of the sample into a buffered diluent. The buffered sample flows through a scavenger stage wherein glucose that may be initially present in the sample is removed. Glucose is a product to be generated from the sample in the determination of α-amylase. Thus, any glucose initially present in the sample must be removed to avoid erroneous results. The scavenger stage comprises two distinct enzyme reactions comprising the reaction of the glucose with a coimmobilized glucose-oxidase catalase reagent, whereby the glucose is converted to gluconic acid and hydrogen peroxide by the glucose oxidase and the hydrogen peroxide is converted to water and oxygen by the catalase. Because hydrogen peroxide is the ultimate product produced in the system to be detected by the detection means in the determination of α-amylase, it is necessary to make certain that the hydrogen peroxide generated from the initially present glucose is removed or destroyed. To assure complete destruction of the hydrogen peroxide, the sample can be passed through an additional immobilized highly purified catalase reagent in the scavenger stage.

The glucose-free sample next flows through a substrate stage wherein the α-amylase present is reacted with an immobilized starch substrate reagent. This stage comprises a quantitative reaction of the α-amylase with a selected starch reagent whereby the starch is hydrolyzed to hydrolysis products, i.e. oligosaccharides, which can be quantitatively converted to glucose in a subsequent stage.

The sample with the oligosaccharides flows through a glucose-generating stage wherein the oligosaccharides are all reacted with immobilized glucoamylase to convert them to glucose. The glucose containing sample flows to a detection stage wherein the glucose is reacted with glucose oxidase to produce gluconic acid and hydrogen peroxide, and the hydrogen peroxide is sensed or detected in detection means.

Reactions of the Procedure

1. Scavenger Stage a.
   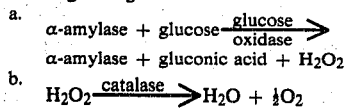
   α-amylase + glucose $\xrightarrow{\text{glucose oxidase}}$
   α-amylase + gluconic acid + H₂O₂ b.
   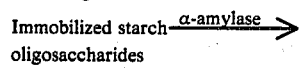
   $H_2O_2 \xrightarrow{\text{catalase}} H_2O + \frac{1}{2}O_2$

2. Substrate Stage

Immobilized starch $\xrightarrow{\alpha\text{-amylase}}$ oligosaccharides

3. Glucose-Generating Stage oligosaccharides $\xrightarrow{\text{glucoamylase}}$ glucose 4. Detection Stage

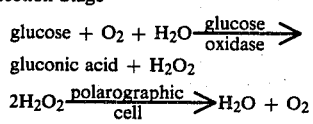
   glucose + O₂ + H₂O $\xrightarrow{\text{glucose oxidase}}$
   gluconic acid + H₂O₂
   $2H_2O_2 \xrightarrow{\text{polarographic cell}} H_2O + O_2$

Scavenger Stage

As stated heretofore, the sample to be tested probably contains glucose and it is necessary to remove any initially present glucose. In testing biologic samples such as blood and urine, substantial amounts of glucose are present and will give erroneous results if the interfering glucose is not removed or compensated for in an initial stage, because in subsequent stages glucose is generated in the present procedure which is the quantitative equivalent of the α-amylase present in the sample.

The scavenger stage in accordance with this invention is designed to remove the interfering glucose of the sample and comprises the use of immobilized enzymes as a reagent which reacts with the interfering glucose and neutralizes it in or removes it from the sample. Particularly preferred is a coimmobilized glucose oxidase-catalase reagent wherein the glucose oxidase initially converts the interfering glucose in the sample to gluconic acid and hydrogen peroxide, and the catalase then converts the hydrogen peroxide to water and oxygen. The gluconic acid, water and oxygen are relatively inert species with respect to the detection means in the subsequent detection stage. It is necessary that all the hydrogen peroxide generated from the interfering glucose be removed because H₂O₂ is detected in the detection stage from subsequently produced glucose. To assure that all the H₂O₂ is removed, the sample can be passed through a second immobilized catalase reagent in the scavenger stage wherein the catalase can be of a highly purified nature.

Immobilized Starch Substrate Stage

The sample from the scavenger stage free of interfering glucose and H₂O₂ is in a condition where the contained α-amylase can be quantitatively determined. This is accomplished by reacting the α-amylase in the sample with an immobilized starch substrate to produce, quantitatively, starch fragments, i.e. oligosaccharides which will be a proper index of the measurable α-amylase activity. The α-amylase reacts with and breaks down starch molecules, but ceases at the α-1,6-glucosidic linkages or branched chain linkages. Accordingly, the starch substrate should desirably be one which has a high reaction rate with α-amylase.

Based on experimentation with various starches, it was found that a starch high in amylose, having mostly straight chains, and containing lower numbers of branched segments would be most suited for the starch substrate. Thus, a starch containing almost completely straight chain α-1,4-glucosidic linkages is preferable. However, the starch should also be capable of being hydrolyzed by the α-amylase to produce oligosaccharides of the desired composition and length. In addition, the starch should be free of materials which can cause competitive enzyme reactions to compete, or interfere with the hydrolysis of the starch by α-amylase.

It was found that wheat, corn and potato starches are among the starches which can be used as the starch substrate in this invention. Particularly preferred is potato starch because it is relatively inexpensive, can be obtained in high purity, resists clumping, has a high ratio of amylose to amylopectin, and contains 75-85% amylose depending on purity, or commercial supplier. Potato starch in addition to having the above desirable properties for the starch substrate, was nearly totally hydrolyzed by α-amylase, producing oligosaccharides which are 2-6 monomers of glucose, with maltose being predominant. The properties and characteristics of the potato starch are well suited for the procedure of this invention and the high ratio of the amylose to amylopectin gives a long lifetime to the substrate reagent, and furthermore, higher yields of measurable glucose from the reaction with α-amylase.

Immobilized Glucose-Generating Stage

The sample from the substrate stage containing the oligosaccharides flows to an immobilized glucose-generating stage wherein the oligosaccharides or starch fragments are quantitatively converted to glucose. The glucose-generating reagent must be capable of removing at least one glucose unit from any fragment, be free of glucose oxidase and catalase (to prevent premature reaction of the generated glucose), and should be suitably immobilized so that it does not leach into the flow stream with the sample.

Several effective glucose-generating reagents are available as a reagent in this flow-through procedure, e.g. maltase, glucoamylase and cellulase. The factors involved in selecting the glucose-generating reagent are stability, reactivity, ease of handling, and ease of purification. Maltase is presently difficult to purify. Cellulases are presently difficult to obtain in pure form and are composed of several different enzymes.

Glucoamylase, unlike the amylases, is able to degrade most naturally occuring starches and their corresponding hydrolysis fragments completely down to glucose, i.e. it hydrolyzes both the alpha-1,4-, and alpha-1,6-glucosidic linkages. The glucoamylase from *Aspergillus Oryzae* has a molecular weight of about 48,000 gm per mole. This enzyme is easy to handle, to purify, and is able to react quantitatively with all the oligosaccharides generated from the starch substrate by the alpha-amylase.

The Detection Stage

The sample from the glucose-generating stage containing the generated glucose flows to a detection stage wherein the glucose is reacted with immobilized glucose oxidase to produce gluconic acid and $H_2O_2$. The $H_2O_2$ generated is passed through a detection means such as a polarographic cell, preferably containing a three electrode system, which furnishes a cell current which is a measure of the glucose under test in the cell. In copending application Ser. No. 477,922, filed June 10, 1974 there is disclosed a method and apparatus for analysis of glucose by oxidation thereof in a bed of immobilized glucose oxidase. The procedures and detection means set forth therein are incorporated herein by reference and can be used in this detection stage for the generated glucose. In addition, U.S. Pat. No. 3,957,592 discloses an apparatus and method for the measurement of a cell current using a polarographic cell which is suitable and adaptable for use with the procedure herein to measure the generated glucose in relation to the quantitative amount of α-amylase in the original sample.

U.S. Pat. No. 3,902,970 discloses another detection cell usable herein, for the measuring of the concentration of glucose in solution, wherein generated $H_2O_2$ is measured in an amperometric cell. The cell has a small bore flow path and includes a cylindrical measuring electrode which carries the sample through its relatively long narrow bore, a counter electrode, reference electrode and a differential amplifier for automatically adjusting the current between the counter and measuring electrodes to maintain the potential between the two electrodes at a predetermined value as fed to one input to the amplifier. The current from the measuring electrode is measured as an indication of the concentration of $H_2O_2$ in the solution and thus the glucose concentration.

In addition to the use of amperometric type detection cells, other suitable types of detection means can be used herein for the measurement of the generated $H_2O_2$. In particular, a spectrophotometer can be used herein as the detection means for measuring the generated $H_2O_2$ as set forth hereinafter.

Immobilized Reagents

The various reagents reacting with the sample containing α-amylase are all immobilized in the various stages. Any of the known methods for immobilizing the enzyme reagents on an insoluble support to form a bed of immobilized reagent can be used in this invention. For example, the glucose oxidase in the scavenger and detection stage can be covalently coupled to a porous glass support with an amino-functional silane coupling agent as disclosed in the article entitled "Immobilized Enzymes: A Prototype Apparatus For Oxidase Enzyme in Chemical Analysis Utilizing Covalently Bound Glucose Oxidase", by M. K. Weibel et. al. appearing in Analytical Biochemistry, 52, 402-414 (1973); glucose oxidase can be immobilized on column packing as in the article entitled, "A New Principle Of Enzymatic Analysis" by H. V. Bergmerey and A. Hagh appearing in Z. Anal. Chem. 261, 333-336 (1972); glucose oxidase can be immobilized in polyacrylic polymers as in the article entitled, "Enzyme Electrodes for Glucose Based on an Iodide Membrane Sensor" by G. Nagy et al appearing in Analytica Chemica Acta, 66, (1973), 443-455; glucose oxidase can be immobilized in a polyacrylamide gel as in the article entitled, "An Enzyme Electrode For The Amperometric Determination of Glucose"]by G. Guilbault et al appearing in Anal. Chem. Acta 64, (1973), 439-455 or U.S. Pat. No. 3,542,662; glucose oxidase immobilized on nickel-silica alumina as in the article entitled, "Immobilization of Glucose Oxidase on Nickel-Silica Alumina" by W. M. Herring et al appearing in Biotechnology and Bioengineering Vol. XIV, pages 975-984 (1972); and glucose oxidase can be immobilized with cyanogen bromide according to the method of U.S. Pat. No. 3,645,852 entitled, "Method Of Binding Water-Soluble Proteins And Water-Soluble Peptides to Water-Soluble Polymers Using Cyanogen Halide", by R. Axen, J. Porath, and E. Ernbach.

In addition to the above, the following patents disclose various immobilization techniques for use in this invention: U.S. Pat. No. 3,933,589 issued to Melvin H. Keyes, Jan. 20, 1976 entitled "Chemical Immobilization of Enzymes"; U.S. Pat. No. 3,839,175 issued to Melvin H. Keyes, Oct. 1, 1974 entitled "Electrodeposition of Enzymes"; and U.S. Pat. No. 3,860,486 issued to Melvin H. Keyes et al, Jan. 14, 1975 entitled "Immobilizing Enzymes With Polystyrene Derivatives". The disclosures of these references are incorporated herein by reference. Thus, in forming the bed of immobilized glucose oxidase the selection of the support from material such as porous glass; particulate and preferably porous refractory oxides such as alumina, titania, zirconia, silica, magnesia, talc, and thoria; glass frit; particulate porcelain; compacted and sintered refractory oxides; clays; water-insoluble polymers; and immobilizing the glucose oxidase thereon by chemical or physical means is well known in the art.

In the scavenger stage, the glucose oxidase and catalase in series are coimmobilized on a suitable support in a flow-through cartridge by the above known methods. As stated previously, a second cartridge can be used in a subsequent scavenger stage. Similarly, in the glucose-generating stage, the glucoamylase can be immobilized as set forth above.

Preferably, the substrate and enzyme reagents of this invention are immobilized by cross-linking them onto porous acid-activated alumina because these immobilization techniques have been well developed and their ease of operation are well-known. Alumina exhibits high durability with moderately high reagent-load capacity, allowing the high flow-rates required for fast analysis of samples in the flow-through procedure of the invention. The use of similar related work with naturally occuring water insoluble substrates has been reported in the literature with a cellulose-cellulase system (Huang, A. A., Biotech. Bioeng., 17, 1421 (1971)), and a physically immobilized acetylcholine system for the measurement of cholinesterase (Guilbault G. G. Anal. Chem. Acta 85, 295 (1976) has recently be reported. These systems combine the soluble enzyme to be assayed with the insoluble substrate, in the bulk aqueous phase and measure the products formed, as for example by pH, potentiometry, thin layer chromatography, etc., as an indication of the quantity of the enzyme assayed. The present invention, takes this process one step further in that the reagents required for the analysis of the products preceeds the substrate-sample through the sample stream, i.e., the product of the first reaction becomes the substrate in the second reaction, etc. Unlike the systems of the above (Huang and Guilbault) being carried out in the bulk phase (i.e. in a well-stirred tank, or beaker), the system of the invention is carried out in the stationary phase with the sample eluting so as to contact each of the immobilized reagents as they are contacted, sequentially, through the flow system. Accordingly, the sequential flow procedure aids in the reduction of certain types of chemical interferences.

In the substrate stage, the starch is preferably immobilized on a porous support in a cartridge through which the sample flows from the scavenger stage cartridges. The immobilized substrate is cross-linked on alumina. It was found that at least about 0.25 gm of immobilized starch was required for continuous flow use for about two weeks or longer.

The intermolecular cross-linking of the reagents on an inorganic support, particularly alumina, is preferred because a non-compressible support allows high flow rates for the samples flowing through the analyzer, is less time consuming, etc.

The immobilized starch substrate is subject to bacterial growth when bulk stored. A storage buffer (0.01 M phosphate, pH 6.0) containing NaCl, $CaCl_2$, and a bacteriostat such as toluene, NaCN or Bio-Ban P-1487, are sufficient to retard bacterial growth if the material is refrigerated.

The preferred arrangement of the immobilized reagents is the sequential arrangement of the reagents in one continuous closed tube or if there is a large amount of reagents, at least two columns can be used. With respect to the columns, the important requirement is that the packed column be permeable to the sample specimen while providing a high surface area to volume ratio to assure adequate contact between the enzyme or substrate reagent and the sample specimen.

Although, the above description of the procedure sets forth the sequential stages as being in order scavenger and then substrate, it is understood that the order can be reversed to produce the same results.

The following Examples further illustrate the invention and disclose the preparation of the various immobilized reagents used in the several stages of the α-amylase determination procedure.

EXAMPLE 1

A 2-50 µl sample of an aqueous buffer suspension (0.025 M Tris-maleate, 0.100 M KCl, $1-6 \times 10^{-4}$ M $CaCl_2$, 1-5% Bio-Ban), containing glucose (0 to 400 mg%), and α-amylase (0 to 10 mg%) (E.C. No. 3.2.1.1), is injected into a flowing buffer stream containing 0.025 M Tris-maleate, 0.10 M KCl, $1.0-6.8 \times 10^{-4}$ M $CaCl_2$, 1-5% Bio-Ban, pH 6.5-7.5. This pH range is selected, because α-amylase shows its greatest catalytic activity in the range 6.5-7.5. The sample then is carried into an immobilized starch reagent by the flowing stream. The α-amylase then hydrolyzes the starch to a series of oligosaccharides, which are relatively low molecular weight polymers of glucose.

These oligosaccharides then flow to a mixing chamber, and are mixed with a second flowing buffer stream (0.10M acetate, 0.05-0.10M KCl, and 1-5% Bio-Ban P-1487, Bio-Ban was obtained from Commercial Solvents Corporation), pH 3.50-4.25. The oligosaccharides then find themselves in a new buffer, by way of the mixing of the two streams. This new buffer is composed of a mixture of the two buffers, dilutes the sample approximately 1:1, and has a pH somewhere between 4.50-6.00. The preferred pH range of the stream flowing out of the mixer is 5.00-6.00, because the remainder of the reagents show optimum catalytic activity in that pH range. These newly buffered oligosaccharides, and sample glucose, if any, then flow into a scavenger. The scavenger is composed of immobilized glucose oxidase (E. C. No. 1.1.3.4) and catalase (E.C. 1.11.1.6) reagent, which converts the glucose to glucono-δ-lactone (which has a rapid equilibration in favor of gluconic acid), and hydrogen peroxide. However, since the amperometric sensor senses hydrogen peroxide, this too must be removed. This is done in an immobilized catalase reagent which converts the hydrogen peroxide to water and oxygen.

After the sample-stream, now composed of the oligosaccharides previously described, flows past the scavenger, they enter an immobilized glucoamylase (E.C. No. 3.2.1.3.) reagent, which converts them to β-d-glucose. This occurs because glucoamylase has:

(1) a hydrolytic aspect, and (2) a transglycolytic aspect, i.e.

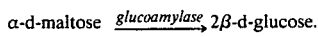

The sample then enters an immobilized highly purified glucose oxidase reagent, particularly free of catalase (which would remove $H_2O_2$, prior to its detection with the amperometric sensor).

The generated $\beta$-d-glucose is then converted catalytically to $H_2O_2$, which is detected by an amperometric sensor, protected from interferences (such as ascorbic acid, uric acid, large molecules, such as proteins, etc.) by the placement of a membrane (MW exclusion limit 12–14,000 gm/mole), placed between the flowing stream, and the sensor. The diffusion characteristics of the membrane allow for the selective determination of $H_2O_2$ over uric acid, ascorbic acid, and other electrochemically active molecules of similar size.

The $H_2O_2$ signal sensed by the amperometric sensor is then transferred to a recorder, and is also placed on a display panel.

EXAMPLE 2

Immobilized Dextranase a. Twenty-five grams of −70+80 mesh porous alumina having an average pore diameter of 0.1 micron, is weighed out, and is washed under two, 250 ml aliquots of distilled, deionized water. This washed alumina is then placed under 200 ml of six normal hydrochloric acid for one hour. The mixture is swirled by hand every 5 to 10 minutes.

b. A 250 mg sample of dextranase (E.C. No. 3.2.1.11, from Dextran Products, Ltd.) is dissolved into 25 ml of five-hundredths molar acetate buffer, pH 5.5. The now dissolved enzyme is centrifuged for one-half hour at 12,000 g's. The resulting precipitate, after decanting off the supernatant, is discarded.

c. Air is evacuated from the pores of the now-acid activated alumina, from step a., above, by placing the solution under an aspirator (or partial vacuum) until no further air bubbles can be seen in the supernatant above the alumina. The evacuated acid-activated alumina is washed with one to two liters distilled, deionized water.

d. The washed alumina, from step c., above, is placed under 50 ml of a 0.05 molar acetate buffer, pH 5.5; and is allowed to swirl, gently, on a laboratory shaker for one-half hour.

e. The decanted enzyme supernatant from step b., above, is added to step d. The mixture is allowed to swirl an additional one-half hour.

f. Five-tenths of a gram of 1-cyclohexyl-3-(2-morpholino-ethyl)carbodiimide metho-p-toluene sulfonate (CMC) purchased from Pierce Chemical Company, is dissolved into 10 ml distilled, deionized water. The mixture is then added to step e., above.

g. Two and a half grams of CMC are dissolved into 25 ml distilled, deionized water; and the resulting solution is added dropwise by a Sigmamotor peristaltic pump overnight, at room temperature, to the mixture of step f., above.

h. The next day, the product is washed under 2 to 3 liters of one-hundredth molar acetate (one-tenth molar in potassium chloride; Mallinkrodt Chemical Works), pH 5.5. The washed product is stored in 10 to 15 ml of this same buffer, under refrigeration, at 0°–4° C.

i. The activity of this material is determined as 3.4 units per milliliter of dextranase-alumina composite. The activity is measured by following the change in oxygen concentration of a 5 ml, 2% starch (potato-Sigma Chemical Company) pH 5.5, 0.01 molar acetate buffer substrate containing 0.12 of a millilter of glucose oxidase (E.C. NO. 1.1.3.4, from Miles Laboratories, Code 31-617).

EXAMPLE 3

Immobilized Starch a. Forty to fifty grams of −40+50 mesh porous alumina, having an average pore diameter of 0.10 u, are weighed out and washed with 1.5 to 3.5 liters of distilled, deionized water until free of fines.

b. The washed alumina is then placed under 200 ml of six normal hydrochloric acid (Lehigh Valley Chemical Company), and is allowed to shake on the laboratory shaker for 16 to 24 hours, at room temperature of about 27.0° C.

c. Five grams of amylose (Sigma Chemical Company, extracted from potato starch) are weighed out and suspended in 100 ml of one millimolar phosphate buffer, pH 6.0.

d. Five to fifteen grams of 'wet' immobilized dextranase (E.C. No. 3.2.1.11), is weighed out. The 5 grams of amylose suspended as in step c., above, are then added to the weighed out quantity of immobilized dextranase. This immobilized dextranaseamylose suspension is allowed to react overnight at room temperature, at pH 6.0.

e. On the next day, the starch suspension is decanted off, and the immobilized dextranase is either discarded, or washed and retained for later use.

f. To the decanted amylose solution is added 5 ml of 0.3 molar potassium hydroxide (J. T. Baker Chemical Company). The resulting alkaline amylose suspension is then all allowed to gently swirl, on the laboratory shaker for one hour.

g. At the end of this time, five-tenths of a milliliter of diaminopropane (Aldrich Chemical Company) is dissolved in 10 ml of methanol (Matheson, Coleman, and Bell Manufacturing Chemists, Inc.), and is added to the alkaline amylose suspension. This mixture is then allowed to swirl gently, on the laboratory shaker for one hour. The now acid-activated alumina (from step b., above) is then placed under an aspirator (or partial vacuum) to remove air from the pores of the alumina for two hours.

h. The evacuated acid-activated alumina is then washed with one or two and a half liters of one normal hydrochloric acid.

i. Then to the washed evacuated acid-activated alumina is added the mixture described in step g., above. This material is then placed on a laboratory shaker, and is allowed to swirl for one hour, at room temperature.

j. To step i., above, is added an additional 5 ml of 0.3 molar potassium hydroxide. The resulting mixture is allowed to swirl gently for an additional one hour.

k. During step j., above, a crosslinking solution is prepared by mixing the reagents in the order as indicated in a 50 ml beaker;

1. Twenty-five hundredths of a milliliter of diaminopropane (Aldrich Chemical Company) into 10 ml of methanol, (Matheson, Coleman, and Bell Manufacturing Chemists, Inc.)
2. One tenth of a milliliter of three-tenths molar potassium hydroxide (J. T. Baker Chemical Company), 3. Fifteen hundredths of a milliliter of dibromoethane (Aldrich Chemical Company), and
4. Ten milliliters of distilled, deionized water.

l. The mixture is prepared in step k., above, is added to step j., above. The resulting mixture is then allowed to cross-link overnight (about 16 to 20 hours) at room temperature (about 27.0° C.), while swirling on the laboratory shaker.

m. On the next day, the product is washed under 2 to 5 liters of one millimolar phosphate buffer, pH 6.0; followed by washing under 2 to 5 liters distilled, deionized water. The now washed amylosealumina composite is then stored, under refrigeration at 0–4° C., in 10 to 20 ml of one millimolar phosphate buffer, pH 6.0.

n. The amount of amylose immobilized by this procedure is found to be 0.099 gram amylose/gram alumina (alternatively expressed as 0.26 gram amylose/ml alumina). This number is obtained by a two-step process. First, the amylose-alumina composite is dried overnight (i.e., 16 to 24 hours), at 100° C. This material is then weighed. Second, the now dried amylose-alumina composite is ignited at 1,000° C. for 2 to 3 hours. The amount of starch bound per gram of alumina is then given by:

$$\frac{\text{Dry Weight at 100° C.(grams)} - \text{Ignited Weight at 1,000° C.(grams)}}{\text{Ignited Weight at 1,000° C.(grams)}}$$

the units are then grams of amylose immobilized per gram of alumina. The grams of amylose bound per milliliter of the amylose-alumina composite is then determined by multiplying this latter value by the density of the alumina, i.e., 2.6.

EXAMPLE 4

Immobilized Glucose Oxidase

Thirty grams of −60+70 mesh, porous alumina having about 0.1μ diameter pore size is seived through an 80 mesh screen for 5 minutes. After the alumina is washed with one liter of distilled, deionized water, it is placed under 200 ml of 6N HCl for one hour. Sufficient glucose oxidase (Sigma Type II) is dissolved in 30 ml of distilled water to give an absorbance of 1.16 at 450 nm and the pH adjusted with 0.1 N HCl or NaOH to pH 7.5. Ten mg of succinic anhydride dissolved in one milliliter of acetone is added to the glucose oxidase solution in 0.1 ml aliquots. One aliquot is added every ten minutes and the solution is stirred for 20 minutes after complete addition. After the alumina is washed of HCl solution and deareated in the presence of 200 ml of distilled water, the wet alumina is mixed with the succinic anhydride treated, glucose oxidase solution. The pH is adjusted to 4.2 and 0.1 gm of 1-ethyl-3-(3-dimethylaminopropyl)-carbodimide HCl (EDC) is added. This combination of materials is allowed to react overnight (16-20 hours) at 0–5° C. with gentle swirling on a laboratory shaker. During this reaction time, a solution of 0.4 gm EDC in 30 ml distilled water is added at the rate of about 0.1 ml/min. The next day, the pH is measured as 5.7, and the absorbance at 450 nm is measured as 0.221. The alumina-glucose oxidase composite is washed with two liters of 0.2 M $(NH_4)_2SO_4$ (enzyme grade Schwartz Mann) followed by 4 liters of distilled, deionized water. The composite is stored in distilled water and the initial activity is measured as 57.7 U/ml of $Al_2O_3$.

EXAMPLE 5

Immobilized Glucose Oxidase

This procedure is the same as described in Example 4 above, except that the glucose oxidase has an initial absorbance of 1.07 and was chromatographed on hexyl hydrophobic gel. The pH of the reaction mixture is measured as 4.1 and the absorbance at 450 nm is measured as 0.261. The initial activity is measured as 24 U/ml of $Al_2O_3$.

EXAMPLE 6

Preparation of Gluclose Oxidase on Hexyl Hydrophobic Gel

Eight grams of Sigma Type II glucose oxidase is dissolved in 10 ml of distilled water and dialyzed overnight against 2mM phosphate buffer, pH 7.0. The resulting solution (approximately 50 ml) is applied to a column of n-hexyl hydrophobic gel (Miles Laboratories, Inc.) (1 cm×30 cm). The column is eluted with 2mM phosphate buffer, pH 7.0, and any protein material eluted is discarded. Next, the column is eluted with 0.05M phosphate buffer, pH 7.0 and the protein eluted contained glucose oxidase which is used for enzyme immobilization as in Example 5.

EXAMPLE 7

Immobilized Catalase a. Twenty to thirty grams of −70+80 mesh porous alumina, as used for the immobilized starch, is weighed out; and is washed under distilled, deionized water until free of fines. This is followed by a 1 liter rinse with 1 normal hydrochloric acid (LeHigh Valley Chemical Company). This acid-rinsed alumina is then placed under 250 to 500 milliliters of 9 normal hydrochloric acid for 1.5 to 3 hours.

b. At the end of this time, the acid-activated alumina is rinsed with 1 liter of 1 molar hydrochloric acid. The acid rinsed acid-activated alumina is then placed under 0.10 normal hydrochloric acid, and the pores of the alumina are evacuated of air by vacuum aspiration for one to two and a half hours.

c. The evacuated acid-activated alumina is then rinsed with 1 liter, 0.01 molar acetate buffer, pH 5.5±0.2, and placed under 100 milliliters of 0.01 molar acetate buffer, pH 5.5±0.2, and is allowed to swirl on the laboratory shaker, at 0–4° C. for 0.5 hour.

d. A quantity of crude glucose oxidase (E.C. No. 1.1.3.4., from Aldrich Chemical Company) is chromatographed on an omega amino decyl hydrophobic gel by a procedure similar to example 6. The eluant is a 1 mM phosphate buffer pH 6.0. The first eluted peak is collected, and retained for immobilization and is added to the final mixture in step c., above. This mixture was allowed to swirl gently on the laboratory shaker for an additional 0.5 hour.

e. A cross-linking solution is prepared, by adding to 10 ml of spectral quality methanol (Burdick and Jackson) placed in a 100 ml beaker, the following reagents in the order indicated:

1. Two-tenths of a milliliter of diaminopropane (Aldrich Chemical Company)

2. One-tenth of a milliliter of dibromoethane (Aldrich Chemical company)
3. Fifteen-hundredths of a milliliter of concentrated hydrochloric acid (Lehigh Valley Chemical Company.), and
4. Fifty milliliters of 0.01 molar acetate buffer pH 5.5. The cross-linking solution is then allowed to stir for 0.5 hour on a magnetic stirrer.

f. The contents of step e., above, are then added to the final contents of the mixture in step d., above; slowly over a 0.5 hour period. The mixture is then allowed to react overnight at 0–5° C., while swirling on the lab shaker, in a water bath.

g. The next day, the final product is washed under 2 to 3 liters of 0.01 molar acetate (0.1 molar in sodium chloride, from Matheson, Coleman, and Bell Manufacturing Chemists, Inc.), pH 5.5. The washed product is then stored under 10 to 15 ml of this same buffer, under refrigeration at 0–4° C.

h. The activity of this material in an 88 $^{mM}$ hydrogen peroxide, 0.01 molar acetate, pH 5.5 substrate-buffer solution is measured by following its increase in oxygen content as a function of time, after the immobilized enzyme is first added to 5 ml of the buffer solution, and the substrate quickly added. Using this procedure the activity is measured as 58$^U$ of catalase per milliliter of the alumina-catalase composite.

EXAMPLE 8

Immobilized Glucoamylase a.–c. Same as in Example 7., above, the immobilization of catalase.

d.
1. Thirty grams of crude glucoamylase (Aspergillus Oryzae, Sigma Chemical Company), are dissolved in 100 ml of 0.01 molar phosphate buffer, pH 7.0. The resulting solution is allowed to stir for 0.5 hour.
2. The resulting suspension, from 1., above, is centrifuged at 5,000 revolutions per minute (3,020 g's), on the RC2-B Sorvall Ultracentrifuge, for 0.5 hour.
3. The supernatant of 2., above, is decanted off, and retained for immobilization, while the precipitate is discarded.
4. The decanted supernatant of 3., above, is then filtered through a 0.22 micron plain, uncoated filter (from Millipore Corporation), using an Antilia ® Hand Pump (Sheleicher and Schuell, Inc.)
5. The supernatant from 2., above, is chromatographed on a Sephadex G-100 (Pharmacia Fine Chemicals) column (90 cm × 5 cm) at a flow-rate of one hundred thirty six milliliters per hour. The entire second peak fraction eluting off is selected for immobilization.

e.–g. Same as the Example 7., the immobilization of catalase.

h. The activity of this immobilized enzyme, although not directly measured can be estimated by measuring the rate of decrease in oxygen content in the presence of excess glucose oxidase. The activity of the crude, soluble enzyme on 0.01 molar maltose (acetate buffer, 0.01M, pH 5.5) is measured as 1.4 units per mg. of protein present. Chromatographic data on G-100 has indicated that about 35% of the crude enzyme is active protein, and adsorption data indicates that 45% of the active chromotographed enzyme is bound to the alumina. Thus, the estimated activity per ml of alumina is:

$$\text{Activity} = \frac{(\delta Al_2O_3)(C_{enz}^{280})(V_{enz}^{Imb})(\frac{\% \text{ enz bound}}{100})(\% \text{ protein})(\text{Activity } ENZ)}{\text{Initial Weight of } Al_2O_3 \text{ grams}} =$$

$$(2.6 \frac{\text{gm } Al_2O_3}{\text{ml } Al_2O_3})(46.56 \frac{\text{mg enz}}{\text{ml}})(10 \text{ ml})(0.45)(0.35)(1.40 \text{ U/mg enz}) =$$

9.0 U/ml glucoamylase-alumina composite, alternatively, the amount of glucoamylase bound is equal to:

$$\frac{(46.56 \text{ mg/ml})(10\text{ml})(0.45)(0.35)}{30 \text{ gm of alumina}} = 2.44 \text{ mg glucoamylase bound per gram of alumina.}$$

EXAMPLE 9

Immobilization of the Starch

Fifty to 250 grams of remeshed porous alumina, (−50+60 mesh) is weighed out, and washed thoroughly with distilled, deionized water (1 to 3 liters) until free of fines. The washed alumina is then rewashed under 0.5 M HCl (1 liter). The alumina is then placed under 250 to 500 ml of 9 M HCl for 1.5 to 3.0 hours, at room temperature, with occasional swirl every 5 to 10 minutes. This now acid-activated alumina is then washed under 2 liters of 0.01 to 0.05 M acetate buffer, pH 5.6. This material is then placed under 250 to 500 ml of 0.01 M acetate buffer, pH 5.6 (or distilled deionized water) and the pores evacuated of air by aspiration at room temperature for 0.5 hour.

The supernatant is decanted off. Then the mixture is again brought to a volume of 250 ml with distilled, deionized water. To this is added 25 gm of sodium sulfate, and stirring with an overhead stirrer is commenced, until the sodium sulfate is completely dissolved.

After the sodium sulfate is dissolved, 6 grams of NaOH pellets are added, and stirred until dissolved. Then slowly over a 1.5 to 3.5 hour period 25 to 35 grams of amylose is added with gentle stirring by the overhead stirrer, so as to not break up the alumina particles. This mixture is then allowed to stir an additional 0.5 to 1 hour after all the starch is added. The solution is checked for clumps or lumps of starch, which are broken up if present.

Then to the now moderately stirring mixture is added 16.70 ml of epichlorohydrin, and the mixture is allowed to react overnight (12 to 20 hours), at room temperature.

On the next day, the alkaline solution is neutralized, i.e., brought to pH 7.0 with 0.5 M HCl. The resulting insoluble reagent product is washed with 3 to 4, 2 liters aliquots of distilled, deionized water, until no starch could be seen in the supernatant above the alumina-starch composite. The final product is then stored under 0.01 M acetate buffer, pH 5.6, containing 5% Bio-Ban, and 0.05 M CaCl$_2$, and 0.01 M NaCl, respectively.

EXAMPLE 10

Crosslinking of Starch Substrate With Diaminopropane and Dibromoethane

Five to 20 grams of starch is weighed out and suspended in a sufficient volume of pH 5.6, 0.01 M acetate buffer, pH 5.6 to make a 2% suspension of starch.

This material (200 to 300 ml) is then placed above 30 to 70 grams of alumina, washed and acid-activated as in Example 9., above.

After adsorbing for 0.5 to 1.5 hours, at room temperature, 25 to 50 ml of a crosslinking reagent:
a. 25 ml methanol,
b. 0.40 ml diaminopropane,
c. 0.25 ml concentrated HCl,
d. 0.20 ml dibromoethane, and
e. 24.05 ml distilled, deionized wter, is prepared.

This crosslinking solution is then added to the adsorbed starch, and allowed to crosslink overnight at room temperature. The resulting immobilized starch is then washed, and stored as in Example 9., above.

EXAMPLE 11

The immobilized starch reagent is prepared as in Example 9. However, prior to washing and storage it is allowed to crosslink with diaminopropane, and dibromoethane as prepared in Example 10., for 3 to 16 hours at room temperature. The resulting material is then washed, and stored as in Example 9.

EXAMPLE 12

Immobilization of the Glucose-Generating Reagent

Twenty-five to 50 grams of porous remeshed alumina, −50+60 mesh, is weighted out, washed thoroughly, and acid-activated as in Example 9. The resulting activated material is placed under 50 ml of 0.01 to 0.05 M acetate buffer, pH 5.6, and set aside for 0.5 to one hour while gently swirling on the laboratory shaker, at, either room temperature, or 0°–4° C.

During this time, 5 to 1,500 mg of, (1) crude enzyme (maltase, glucoamylase, or $\beta$-glucosidase) is weighed out, and dissolved in 25 ml of distilled, deionized water, or buffer, and centrifuged at 10,000 g's for 0.5 hour, or (2) a 40% ammonium sulfate precipitate is collected. In the case of the crude enzymes, the supernatant solution is added to the acid-activated alumina, and allowed to adsorb 0.5 to 1.5 hours. In the case of the 40% ammonium sulfate precipitation, however, the precipitate is redissolved in at least 25 ml of distilled, deionized water, or buffer (0.1 M acetate, pH 5.6), and allowed to adsorb onto the acid-activated alumina for 0.5 to 1.5 hours.

After the adsorption process is completed, a crosslinking reagent composed of diaminopropane and dibromoethane as in Example 10., is prepared and added. The reaction is allowed to continue overnight, at room temperature, while swirling on the laboratory shaker. Washing and storage is as in Example 9.

Figure 2:
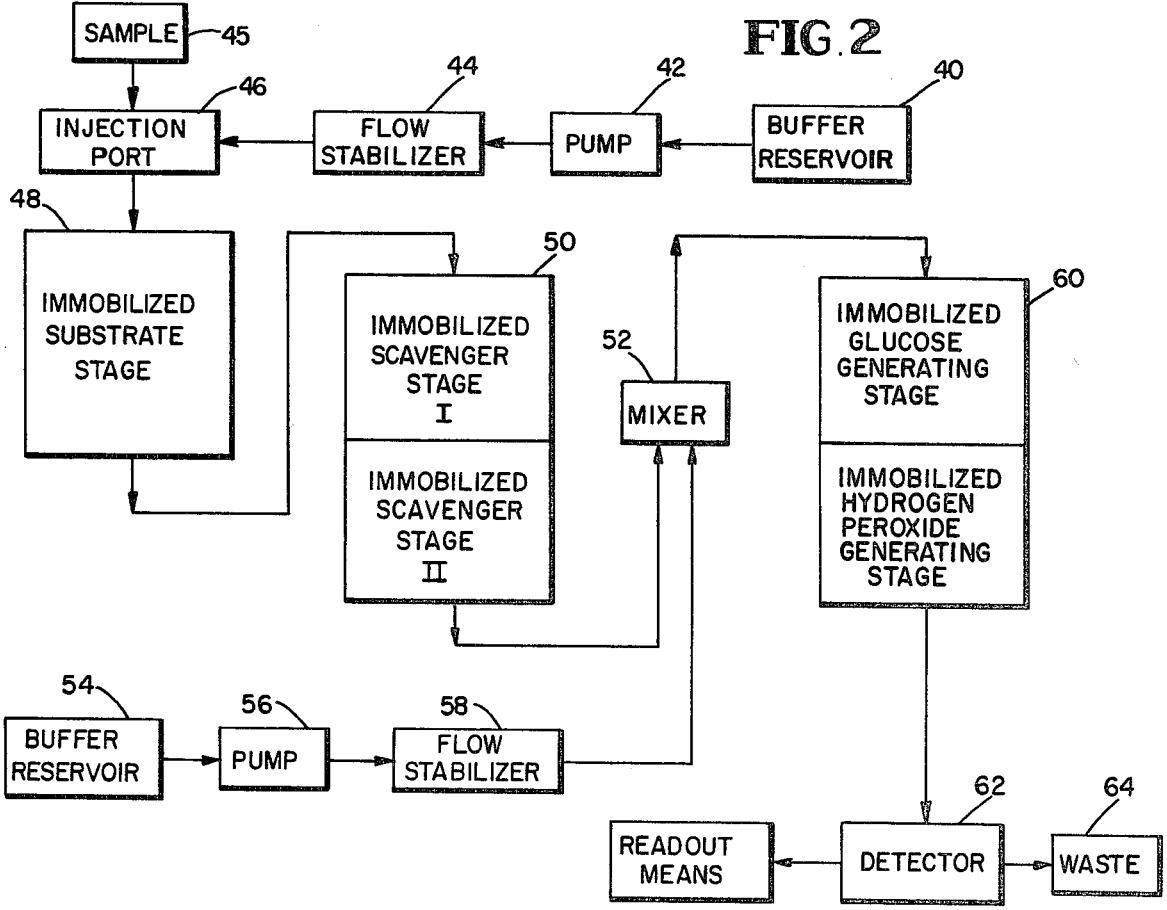

In the following Examples, reference is made to the drawings forming a part of this application in which:

FIG. 1 is a diagram of a continuous stream of the invention as applied to the measurement of $\alpha$-amylase contained in a solution sample; and FIG. 2 is a diagram of a split stream system of the invention as applied to the measurement of $\alpha$-amylase contained in a solution sample. Neither FIG. 1 nor FIG. 2 are drawn to scale and do not indicate the proportion of reagents actually used. However, Table I sets forth the amounts of immobilized reagent which can be used in the Examples of the procedures of FIG. 1 and 2.

TABLE I

AMOUNTS OF REAGENTS USED IN THE EXAMPLES

A. Applicable to Example 17 (FIG. 1)

| Immobilized Reagent | Amount of Reagent Present (ml) | | Referenced to Examples |
|---|---|---|---|
| | Amperometric Detection Means | Spectrophotometric Detection Means | |
| Scavenger | 0.66 | 0.47 | 13 |
| Substrate | 1.50 | 0.44 | 14 |
| Glucoamylase | 0.95 | 0.21 | 15A |
| Alpha-Amylase | 0.65 | 0.25 | 15B |
| Maltase | 1.06 | 0.45 | 15C |
| Glucose Oxidase | 0.85 | 0.48 | 16 |

B. Applicable to Example 22 (FIG. 2)

| | | | |
|---|---|---|---|
| Substrate | 8.00 | — | 18 |
| Scavenger, Part A | 2.00 | — | 19A |
| Scavenger, part B | 1.00 | — | 19B |
| Glucoamylase | 3.00 | — | 20B |
| Glucose Oxidase | 2.00 | — | 21 |

Referring to FIG. 1, the continuous stream system shown therein comprises a buffer reservoir 10 from which a buffered solution is pumped by a pump 12 into an injection port 14. A sample solution 16 containing $\alpha$-amylase to be quatitively determined in the system is injected into the buffered solution in the injection port 14. The buffered sample solution stream flows into a column 18 containing immobilized reagents in sequence, i.e. immobilized scavenger reagent 20, immobilized substrate 22 such as amylose, immobilized glucose-generating reagents such as glucoamylase, 24, immobilized $\alpha$-amylase 26, immobilized maltase 28, immobilized hydrogen-peroxide-generating reagents 30 such as glucose oxidase. The sample stream containing the hydrogen peroxide generated flows to a hydrogen peroxide detector 32 such as a spectrophotometer or amperometric cell. The spent sample is passed to waste 34.

The continuous stream system as set forth in FIG. 1 can be used as set forth hereinafter in Examples 13–17.

Referring to FIG. 2, the split stream system shown therein comprises a buffer reservoir 40 from which a buffered solution is pumped by a pump 42 through a flow stabilizer 44 into an injection port 46. A sample solution 45 containing alpha-amylase to be quantitatively determined in the system is injected into the buffered solution in the injection port 46. The buffered sample solution flows to a column 48 containing an immobilized substrate reagent such as amylose. The sample solution flows from a ccolumn 48 to column 50 containing scavenger reagents and then to a mixer 52. A buffer reservoir 54 contains a second buffer solution which is pumped by a pump 56 through a flow stabilizer 58 to the mixer 52.

The glucose-free sample solution buffered by the second buffer stream flows into a column 60 containing in sequence immobilized glucose-generating reagents and immobilized hydrogenperoxide-generating reagents. The sample stream containing the hydrogenperoxide-generated flows to a hydrogen peroxide detector 62 such as a spectrophotometer or amperometric cell. The spent sample is passed to waste 34.

The split stream system as set forth in FIG. 2 can be used as set forth hereinafter in Examples 18–22.

In the system set forth in FIG. 1, an immobilized alphaamylase has been placed in column 18. The purpose of the immobilized alpha-amylase is to break down relatively larger oligosaccharide fragments, which may come off the immobilized amylose substrate stage, into relatively smaller oligosaccharides which are converted to glucose.

EXAMPLE 13

Preparation of the Scavenger Stage

1. Twenty grams of 35 percent porosity, −50+60 meshed porous alumina (Owens-Illinois) having an average pore size of one-tenth micron, is carefully weighed out.
2. The porous alumina is then washed under 25, 250 ml aliquots of distilled, deionized water.
3. The washed alumina, from step 2., above, is then placed under 150 ml of size normal hydrochloric acid in a 200 ml erylenmeyer flask, for one to one and one-half hours, swirling gently every ten minutes at room temperature.
4. During the acid-activation of the porous alumina discussed in step 3., above, the following solutions are prepared:
    a. A 30 to 40 mm length of dialysis tubing (Spectrapore) having a molecular weight cut-off limit of 6 to 8,000, is obtained and placed in a 200 ml beaker, under 150 ml of 1/100 molar maleate buffer, pH 5.6, and refrigerated at 0° to 4° C. for half to one hour.
    b. A cross-linking solution is prepared by dissolving two grams of CMC, i.e., 1-cyclohexyl-3 (2-morpholinethyl)carbodiimide metho-p-toluene sulfonate into ten milliliters distilled, deionized water, and allowed to stir one hour, at room temperature.
    c. Twenty milliliters of glucose oxidase (Miles Research Laboratories, code 31-617) is measured out, and 26 mg. succinic anhydride is added. The resulting mixture is allowed to react for at least 40 minutes at room temperature.
5. At the end of the acid-activation time indicated in step (3), above, the alumina is rinsed by rapid swirling under three, one-hundred fifty milliliters aliquots of distilled, deionized water.
6. The alumina is then placed under one-hundred fifty milliliters distilled, deionized water, and deaerated for one hour at room temperature. The flash is swirled gently every ten minutes.
7. At the end of step (6), above, the supernatant solution is carefully decanted off, and discarded. To the alumina remaining is added the solution prepared in step 4. (b) above.
8. A knot is tieed in one-end of the dialysis tubing from step 4. (a), above.
9. Into the dialysis bag is added the mixture described in step (7), above.
10. Then the solution prepared in step 4. (c), above, is also added to the dialysis bag, and the open end is then sealed by tying a knot.
11. The closed dialysis bag containing the reactants from step (10), above is then placed under one-hundred fifty milliliters, distilled, deionized water in a two-hundred milliliter flask. This beaker is then placed on a laboratory shaker water bath at zero to six degrees centigrade for twelve to sixteen hours.
12. After step (11), above, the material is removed from the dialysis bag, and is washed under one liter distilled, deionized water, and is refrigerated at zero to four degrees centigrade, under ten milliliters of one-one-hundredth molar maleate buffer, pH 6.0.
13. The activity of the final product is measured:
    a. Glucose oxidase activity is measured in a $5 \times 10^{-2}$M $\beta$-d-glucose (Sigma Chemical Company) solution, buffered to pH 5.6 with 0.01M acetate buffer. The glucose oxidase activity is found to be 69 U per ml of porous alumina-enzyme composite.
    b. Catalase activity is measured in a 1% hydrogen peroxide solution, buffered to pH 5.6 with 0.01 M acetate buffer. The catalase activity is found to be 59 U per ml of porous alumina-enzyme composite.

EXAMPLE 14

Preparation of the Immobilized Starch Substrate Stage

1. Thirty grams of 1/10 micron pore size, 35% porosity, porous alumina is carefully weighed out.
2. The alumina of step 1., above, is then washed under five two hundred ml aliquots of 5/10 molar hydrochloric acid
3. After washing, the alumina is placed under 200 ml of six normal soddium hydroxide for one and one-half hours and allowed to stir gently with a magnetic stirrer.
4. During step 3., above, 5 grams of potato amylose (Sigma Chemical Company) is suspended in 75 ml of 1/10 molar acetate buffer, pH 5.7, and is set aside while gently stirring for the time being.
5. The alumina from step 3., above, is then washed under 500 ml of 1/10 molar acetate buffer, pH 5.7, and is placed under 200 ml of 1/10 molar acetate buffer, pH 5.7, and is allowed to stir gently for ½ hour, with a magnetic stirrer, at room temperature.
6. The contents of step 4., above, is added to the contents of step 5., above, and stirring is allowed to continue, an additional ½ hour at room temperature.

The remaining steps of this procedure is carried out under the hood.

7. Sufficient six normal sodium hydroxide is added to step 6., above, to bring the pH of the mixture to 11.50.
8. Four grams cyanogen bromide is weighed out, quickly crushed with a mortar and pestle, and is quickly added to the pH adjusted mixture of step 7., above. The time for weighing and grinding before addition of the cyanogen bromide is not to exceed ninety seconds.
9. Excess cyanogen bromide is neutralized by excess sodium hydroxide.
10. Then during the first 90 seconds of the reaction of step 8., above, aliquots of six normal sodium hydroxide is added to maintain the pH of the mixture at 11.50.

11. During step 7., above, 15/100 ml diaminopropane and 2/10 ml dibromoethane dissolved in five ml of spectral grade methanol is added to the mixture of step 10., above. The pH is being maintained at pH 11.50 with six normal sodium hydroxide.

12. The reaction of the materials in step 11., above, is allowed to continue for one hour at room temperature.

13. The final product is then washed with several volumes of distilled, deionized water.

14. The amount of starch insolubilized in this manner, is determined as approximately 0.112 gram of amylose per grams of porous alumina-starch composite, by gravimetric means.

EXAMPLE 15

Preparation of the Glucose Generating Stage

NOTE: After the enzyme in step 2. of each of the following procedures has been suspended, and prior to refrigeration, each sample is centrifuged at 10,000 revolutions per minute (12,350 gravities), for ½ hour. The supernatant is decanted off, and retained for immobilization, while the precipitate is discarded.

A. Preparation of Immobilized Glucoamylase
(Biological Source: *ASPERGILLUS ORYZAE*)

1. Twenty-eight grams of prewashed, minus forty plus fifty meshed, porous alumina is weighed out, and placed under six normal hydrochloric acid, for 1½ hours at room temperature, swirling the contents every 15 to 20 minutes.

2. 250 mg crude glucoamylase (Sigma Chemical Co.) is weighed out, and suspended in 25 ml, 5/100 molar acetate buffer, pH 5.5, and refrigerated at zero to 4° C. until ready to use.

3. The material of step 1., above, is then rinsed under four aliquots of distilled, deionized water. Each aliquot of water is 250 ml. It is then deaerated under 150 ml of 5/100 molar acetate buffer, pH 5.5 for one hour, at room temperature.

4. The supernatant of step 3., above, is then decanted off and discarded. The remaining alumina is placed under 50 ml of 5/100 molar acetate buffer, pH 5.5.

5. The solution from step 4., above, is then placed in cold water bath, on a laboratory shaker, at zero to 4° C., and is allowed to shake undisturbed for at least ½ hour.

6. While step 5., above, is going on, dissolved into 25 ml of distilled, deionized water, two-and-a-half grams CMC, i.e., 1-cyclohexyl-3(2-morpholineothyl)-carbodiimide metho-p-toluene sulfonate.

7. The solution prepared in step 6., above, is then allowed to stir gently for 45 minutes, at room temperature (about 27° C.)

8. To the material of step 5., above, is added the contents from step 2., above. The mixture is then allowed to adsorb undisturbed, for at least ½ hour at zero to 4° C.

9. At the end of the adsorption time indicated in step 8., above, the solution from step 6., above, is added by pump to the solution of step 8., above. The addition of the crosslinking reagent is at a rate of 5/100 to 1/10 milliliter per minute.

10. The mixture of step 9., above, is then allowed to react for 12 to 16 hours, at zero to 4° C.

11. The final product, is then washed with three 250 ml volumes of 15/100 molar ammonium sulfate, followed by three, 250 ml volumes of distilled, deionized water. The final washed material is then stored under 10 ml, 5/100 molar acetate buffer, pH 5.5, under refrigeration at 0° to 4° C.

12. The activity of this immobilized glucoamylase is measured as 7.86 units per milliliter of alumina-glucoamylase composite, in a 1/100 molar maltose solution, in 1/100 molar acetate buffer, pH 5.5.

B. Preparation of Immobilized Alpha-Amylase
(Biological Source: MALT)

1. Twenty-eight grams of prewashed, minus 40 plus 50 meshed, porous alumina is weighed out, and placed under six normal hydrochloric acid, for 1½ hours, at room temperature, swirling the contents every 15 to 20 minutes.

2. 270 mg crude α-amylase (Sigma Chemical Co.) is weighed out, and suspended in 25 ml, 5/100 molar acetate buffer, pH 5.5 and refrigerated at 0° to 4° C. until ready to use.

3. The material of step 1., above, is then rinsed under four aliquots of distilled, deionized water. Ech aliquot of water is 250 ml. It is then deaerated under 150 ml, of 5/100 molar acetate buffer, pH 5.5, for one hour at room temperature.

4. The supernatant of step 3., above, is then decanted off, and the remaining alumina is placed under 50 ml of 5/100 molar acetate buffer, pH 5.5.

5. The solution from step 4., above, is then placed in a cold water bath, on a laboratory shaker, at 0° to 4° C., and is allowed to shake undistrubed for at least one-half hour.

6. While step 5., above, is continuing, dissolve into 25 ml of distilled, deionized water, two-and-a-half grams CMC, i.e. 1-cyclohexyl-3(2-morpholinethyl)-carbodiimide metho-p-toluene sulfonate.

7. The solution prepared in step 6., above, is then allowed to stir gently for 45 minutes at room temperature (about 27° C.).

8. To the material of step 5., above, is added the contents of step 2., above. The mixture is allowed to adsorb undisturbed for at least one-half hour at 0° to 6° C., on the laboratory shaker.

9. At the end of the adsorption time indicated in step 8., above, the solution from step 6., above, is added by pump to the solution of step 8. This addition of the crosslinking reagent is at a rate of 5/100 to 1/10 ml per minute.

10. The mixture of step 9., above, is then allowed to react for 12 to 16 hours, at 0° to 6° C.

11. The final product, is then washed with three 250 ml volumes of 15/100 molar ammonium sulfate, followed by three 250 ml volumes of distilled, deionized water. The final washed material is then stored under 10 ml 5/100 molar acetate buffer, pH 5.5, under refrigeration at 0° to 4° C.

12. The activity of this immobilized alpha-amylase reagent is measured as 7.98 Units per ml of alumina-alpha-amylase composite, in a 2% potato starch (Sigma Chemical Co.) suspension in 1/100 molar acetate buffer, pH 5.5.

C. Preparation of Immobilized Maltase
(Biological Source: *ASPERGILLUS NIGER*)

1. Twenty-six grams of prewashed, minus 40 plus 50 meshed, porous alumina is weighed out, and placed under six normal hydrochloric acid, for one-and-a-half hour, at room temperature, swirling the contents every 15 to 20 minutes.

2. 275 mg of crude maltase (Sigma Chemical Co.) is weighed out, and dissolved (suspended) in 25 ml of 5/100 acetate buffer, pH 5.5, and refrigerated at 0° to 4° C. until ready to use.

3. The material of step 1., above, is then rinsed under four aliquots of distilled, deionized water. Each aliquot of water is 250 ml in volume. It is then deaerated under 150 ml of 5/100 molar acetate buffer, pH 5.5., for one hour, at room temperature.

4. The supernatant of step 3., above, is decanted off and discarded and the remaining alumina is placed under 5 ml of 5/100 molar acetate buffer, pH 5.5.

5. The solution from step 4., above, is then placed in a cold water bath, on a laboratory shaker, at 0° to 4° C., and is allowed to shake undisturbed for at least one-half hour.

6. While step 5., above, is in progress, dissolve into 25 ml of distilled, deionized water, two-and-a-half grams CMC, i.e. 1-cyclohexyl-3(2-morpholinethyl)-carbodiimide metho-p-toluene sulfonate.

7. The solution prepared in step 6., above, is then allowed to stir gently for 45 minutes on a magnetic stirrer, at room temperature.

8. To the material from step 5., above, is added the contents of step 2., above. The mixture is allowed to adsorb (react) undisturbed for at least one-half hour at 0° to 6° C. on the laboratory shaker.

9. At the end of the adsorption time indicated in step 8., above, the solution from step 6., above, is added by pump to the solution of step 8., above. The addition takes place at a rate of 5/100 to 1/10 ml per minute.

10. The mixture of step 9., above, is then allowed to react for 12 to 16 hours, at 0° to 6° C.

11. The final product, is then washed with three 250ml volumes of 15/100 molar ammonium sulfate, followed by three 250 ml volumes of distilled, deionized water. The final washed material is then stored under 10 ml 5/100 molar acetate buffer, pH 5.5, under refrigeration at 0° to 4° C.

12. The activity of this immobilized maltase reagent is measured as 10.30 Units per ml of alumina-maltase composite, in a 1/100 molar maltose solution, buffered to 1/100 with acetate buffer, pH 5.5.

EXAMPLE 16

Preparation of the Hydrogen Peroxide Generating Stage (Detection Stage)

1. Twenty grams, −70+80 meshed alumina is washed under two and a half liters distilled, deionized water until free of fines, or the supernatant remains clear, in ten, 250 ml aliquots.

2. The washed alumina of step 1., above, is placed under 250 ml six normal hydrochloric acid for one hour at room temperature.

3. 100 mg. Glucose oxidase (Biological source: *Aspergillus Niger*, Worthington Biochemical Corporation) is dissolved in 50 ml of a 3/10 molar solution of sodium chloride. The pH is adjusted carefully to pH 4.0 with a one normal solution of hydrochloric acid.

4. Ten milligrams of succinic anhydride is added to the solution prepared in step 3., above, and is allowed to react, while stirring gently for 40 minutes at room temperature.

5. The acid-activated alumina of step 2., above, is washed by hand swirling in a 500 ml vacuum flask with distilled, deionized water, until the supernatant is clear.

6. The washed alumina from step 5., above, is placed under 200 ml of distilled, deionized water, and deaerated for one hour. At the end of the hour, the supernatant is discarded.

7. The procedure of step 6., above, is repeated two more times.

8. The glucose oxidase solution of step 4., above, is then added to the deaerated alumina of step 7., above.

9. To the solution of step 8., above, is added one gram of CMC, i.e. 1-cyclohexyl-3(2-morpholinethyl)-carbodiimide metho-p-toluene sulfonate crystals.

10. The pH of the solution is then adjusted to pH 4.0.

11. Dissolve into 40 ml distilled deionized water one-and-a-half grams CMC (see step 9., above).

12. The solution prepared in step 11., above, is added at a rate of 1/10 ml per minute, by pump, to the mixture prepared in step 9., above.

13. The reaction of step 12., above, is then allowed to continue for 12 to 16 hours, at 0° to 5° C., on the laboratory shaker.

14. The final product is washed with two liters 2/10 molar acetate buffer, pH 5.5.

15. The preparation is then stored under 10 to 15 ml of 1/100 molar phosphate buffer, pH 6.5, and is stored in the refrigerator at zero to 4° C.

16. The activity of this final product is measured:
   a. The glucose oxidase activity in a 1/100 molar β-d-glucose (Sigma Chemical Company) solution, buffered to 1/100 molar acetate, pH 5.5, is measured as 90 units per milliliter of alumina-glucose oxidase composite.
   b. The coimmobilized catalase activity in a one percent hydrogen peroxide (Fisher Scientific Company) buffered to 1/100 molar acetate, pH 5.5, is measured as four Units per milliliter of alumina-glucose oxidase composite.

EXAMPLE 17

Continuous Stream Alpha-Amylase Determination

An aqueous solution of α-amylase (hog pancreas, Sigma Chemical Company) is either:
  a. injected into a flowing stream, or
  b. added to an eluant, that is 1/10 molar acetate buffer, The α-amylase flows into a scavenger stage (See Example 13) composed of coimmobilized glucose oxidase and catalase, and is cleaned of contaminating sample glucose as follows:

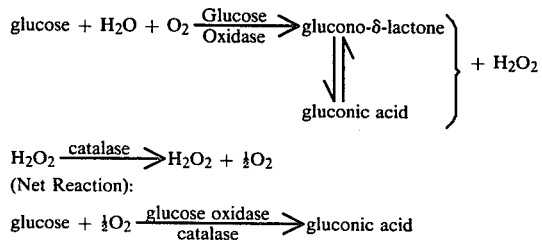

(Net Reaction):

$$glucose + \tfrac{1}{2}O_2 \xrightarrow[\text{catalase}]{\text{glucose oxidase}} gluconic\ acid$$

The now glucose-free α-amylase solution then flows into an insoluble substrate reagent, composed of immobilized potato amylose (see Example 14), and hydrolyzes the starch into various oligosaccharides. The next stage is required to break these oligosaccharides down to glucose.

These oligosaccharides then flow through an insoluble glucose generating stage (see Example 15), composed sequentially of immobilized glucoamylase, alpha-amylase, and maltase, to generate larger yields of glucose as follows:

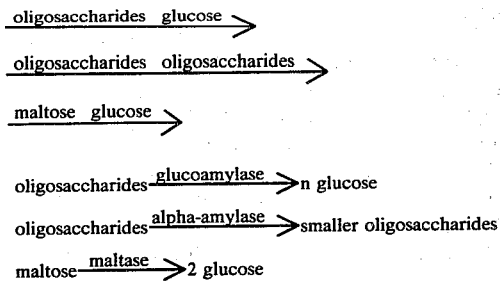

The glucose generated is a quantitative measure of the alpha-amylase injected into the system. The use of the enzymes in the glucose generating stage is to result primarily in larger signals being detected.

The generated glucose then flows into a hydrogen peroxide generating stage (see Example 16) composed of immobilized highly purified glucose oxidase:

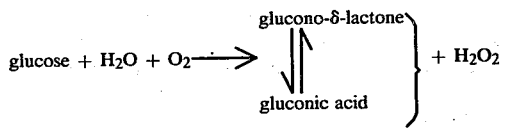

The hydrogen peroxide generated is detected by following the absorbance at 240nm for hydrogen peroxide. Although the detector here is a spectrophotometer, the linear result correlates well with an amperometric sensor device, as will be seen hereinafter.

EXAMPLE 18

Preparation of the Immobilized Substrate Reagent

1. Fifteen hundred milligrams of potato amylose (Sigma Chemical Co.) is weighed out, and suspended in 200 ml of 1/100 molar acetate buffer, pH 5.6, containing 5/100 molar potassium chloride.

2. The mixture prepared in step 1., above, is allowed to stir gently with a magnetic stirrer, at room temperature (about 27° C).

3. After approximately one-half hour, 2.70 gm imidazole is added to the gently stirring mixture prepared in step 2., above.

4. The mixture prepared in step 3., above, is then allowed to stir at a more rapid rate for 12 to 16 hours, at room temperature.

5. During step 4., above, 75 grams of −50+60, re-screened, porous alumina is weighed out, and placed under 1.70 M hydrochloric acid.

6. The mixture prepared in step 5., above, is then placed on the laboratory shaker, at room temperature, and is allowed to swirl for 12 to 16 hours undisturbed.

7. After the appropriate time in step 6., above, has elapsed, the mixture is then deaerated for one hour.

8. The deaerated porous alumina is then washed under distilled, deionized water, until the supernatant is clear. The supernatant is decanted off, and discarded. The alumina is returned to the laboratory shaker.

9. Over the washed, deaerated alumina (see step 8., above), the solution prepared in step 4., above, is added over a half hour period, while being swirled on the laboratory shaker.

10. After all the amylose has been added, the mixture of step 9., above, is allowed to swirl undisturbed for 2 hours at room temperature.

11. The following crosslinking solution is quickly prepared:
 a. 20 ml of methanol,
 b. to a. above, is added ½ ml of diaminopropane,
 c. to b. above, is added 25/100 ml dibromoethane,
 d. to c. above, is added 2/10 ml concentrated hydrochloric acid, and
 e. to d. above, is added 10 ml distilled, deionized water.

12. The mixture prepared in step 11., above, is added immediately to the final mixture of step 10., above.

13. The reaction of step 12., above, is allowed to continue for 12 to 16 hours, at room temperature, while stirring on the laboratory shaker.

14. The final product from step 13., above, is washed under 15, 200 ml volumes of distilled, deionized water.

15. The washed product of step 14, above, is stored under 10 to 15 ml of 1/100 molar acetate buffer, pH 5.6, 5/100 molar in potassium chloride, and 1/10,000 molar in sodium cyanide as an antibacterial agent. The product is stored at 0° to 4° C., in the refrigerator until ready for use.

16. The amount of starch bound to the porous alumina is determined gravimetrically as 0.105 gm starch per milliliter of starch-alumina composite.

EXAMPLE 19

Preparation of the Two-Stage Scavenger Reagent

A. Preparation of Immobilized Glucose Oxidase

1. Thirty grams of −60+70 meshed porous alumina is weighed out, and sieved through an eighty mesh wire screen for five minutes. The sieved alumina is then washed under distilled, deionized water until the supernatant is clear.

2. The washed alumina is then placed under 200 ml of six normal hydrochloric acid for one hour.

3. Into distilled, deionized water is dissolved sufficient glucose oxidase (Sigma Chemical Company, Type II) to make a solution of absorbance 1.50 at 450 nm. The pH of this enzyme solution is adjusted to pH 7.5. The total volume of the solution is 30 ml.

4. Ten milligrams succinic anhydride is dissolved in one milliliter of spectral grade acetone.

5. One-tenth milliliter of the solution prepared at step 4., above, is added to the enzyme solution of step 3., above, every ten minutes. A 20-minute reaction period is allowed after the final tenth of a milliliter of the solution prepared in step 4., above, has been added.

6. The acid-activated alumina from step 2., above, is then washed with distilled, deionized water until the supernatant is clear.

7. The washed alumina is placed under 200 ml distilled, deionized water, and deaerated for one hour.

8. The activated glucose oxidase from step 5., above, is added to the deaerated alumina of step 7., above, and the pH is immediately adjusted to 4.2.

9. One tenth gram EDC, i.e., 1-ethyl-3-(3-dimethylaminopropyl) carbodiimide hydrochloride is added to the solution prepared in step 8., above.

10. 4/10 of a gram EDC is dissolved in 30 ml distilled, deionized water.

11. The solution prepared in step 10., above, is added to the solution of step 9., above, at a rate of 1/10 ml per minute.

12. The reaction of the materials prepared in step 11., above, is allowed to continue undisturbed, at 0° to 5° C., on the laboratory shaker, for 12 to 16 hours.

13. The final product is washed with 2 liters, 2/10 molar ammonium sulfate, followed by 4 liters distilled, deionized water. The material is then stored under 10 to 20 ml distilled deionized water at 0° to 4° C.

14. The activity of this preparation is found to be:
 a. the activity of glucose oxidase, in a 1/100 molar β-d-glucose (Sigma Chemical Co.) solution, buffered To 1/100 molar acetate, pH 5.6 is measured as 57 Units per milliliter of alumina-glucose oxidase composite.
 b. the activity of catalase, in a 5/100 percent hydrogen peroxide solution, buffered as in 14.a., above, is measured as less than one Unit per milliliter of alumina-glucose oxidase composite.

B. Preparation of the Immobilized Catalase

1. Thirty grams −70+80 mesh porous alumina is weighed out, and washed by hand swirling with distilled, deionized water, until the supernatant is clear. The washed alumina is then rinsed by hand swirling with 15, 200 ml volumes of 1/10 molar hydrochloric acid.

2. The washed alumina from step 1., above, is then placed under 250 ml of six normal hydrochloric acid for 1½ hours at room temperature (approximately 27° C.)

3. The acid-activated alumina is then decanted off the six normal hydrochloric acid supernatant, and rinsed with two, 250 ml volumes of 1/10 M hydrochloric acid.

4. The rinsed acid-activated alumina is then placed under 200 ml 1/10 M hydrochloric acid, and deaerated at room temperature, swirling every ten minutes, for one hour.

5. The supernatant above the deaerated alumina is decanted off, and discarded.

6. The alumina is then placed under 250 ml of 1/100 M acetate buffer, pH 5.5, and is allowed to swirl, undisturbed on the laboratory shaker for at least one hour.

7. Using an omega amino n-decyl hydrophobic column (Miles Yeda, Ltd.), having a radius x length=1.3 cm×38.0 cm, ten grams curde glucose oxidase (Aldrich Chemical Co.) dissolved in 25 ml distilled, deionized water, dialysized against a one millimolar phosphate buffer, pH 6.0, that is 3/100 millimolar in sodium cyanide, is eluded at a flow-rate of ten to 15 ml per hour. The fraction collected in test tube number I and II having a total volume of about 30 ml is selected for insolubilization.

| Test Tube No. | Activity (U/Mg) | |
| --- | --- | --- |
| | Glucose Oxidase[a] | Catalase[b] |
| I | 7.7 | 50.0 |
| II | 10.0 | 62.4 |

[a]Glucose oxidase activity is measured in a 1/100 molar β-d-glucose solution, buffered to 1/100 molar acetate buffer, pH 5.6.
[b]Catalase activity is measured in a ½% hydrogen peroxide solution, buffered as in a., above, at pH 5.6.

8. The material of step 7., above, is added to the solution of step 6., above, and is allowed to react, undistrubed, on the laboratory shaker, at 0° to 6° C. for at least ½ hour.

9. During the adsorption indicated in step 8., above, add a 50 ml of 1/100 molar phosphate buffer, pH 6.0,
 a. ten milliliters spectral grade methanol
 b. 2/10 milliliter diaminopropane
 c. 1/10 milliliter dibromoethane
 d. 15/100 milliliter concentrated hydrochloric acid, and allow to stir undisturbed on a magnetic stirrer for half hour, at room temperature.

10. The contents from step 9., above, is added to the contents of step 8., above, in equal volume aliquots, over a half hour period.

11. The mixture prepared in step 10., above, is allowed to react for 12 to 16 hours, at 0° to 4° C. on the laboratory shaker.

12. The final product is washed under two liters, 1/100 M acetate buffer, pH 5.5, which is 1/10 molar in sodium chloride followed by a two liter wash with distilled, deionized water.

13. The washed final product is then stored under 15 ml 1/100 M acetate buffer, pH 5.5, that is 3/100 millimolar in sodium cyanide.

14. The activity of this material in an 88 mM hydrogen peroxide, 0.01 M acetate, pH 5.5 substrate-buffer solution is measured as 59 Units of catalase per milliliter of the alumina-catalase composite, with negligible glucose oxidase activity.

EXAMPLE 20

Preparation of Immobilized Glucoamylase

A. Preparation of Immobilized Purified Glucoamylase

1. Twenty grams −70+80 mesh, rescreened, porous alumina is weighed out, and first washed under distilled, deionized water until free of fines, and then washed under 500 ml, 1/10 M hydrochloric acid.

2. Fifty grams crude glucoamylase (Sigma Chemical Company, Aspergillus Oryzae) is dissolved in 100 ml of 1/100 M phosphate buffer, pH 6.0, and centrifuged at 12,300 gravities for one hour in an ultra centrifuge. The resulting insoluble precipitate is discarded.

3. The supernatant from step 2., above, is chromatographed on a Sephadex G-200 (Pharmacia Fine Chemicals) column (6 cm×0.7 cm) at a flow-rate of 136 ml per hour. The entire second peak fraction eluting off is selected for immobilization.

4. The washed alumina of step 1., above, is then placed under 250 ml of 9 normal hydroxhloric acid and is allowed to swirl, undisturbed, at room temperature for 1½ hours.

5. The alumina is then washed twice, under 500 ml of 1/10 M hydrochloric acid followed by a 500 ml aliquot wash of 1/100 M phosphate buffer, pH 6.0.

6. The washed alumina is then placed under 50 ml of 1/100 M phosphate buffer, pH 6.0, and is allowed to swirl, undistrubed, for at least half hour at room temperature, on the laboratory shaker.

7. To the mixture prepared in step 6., above, is added the entire contents of step 3., above.

8. The mixture prepared in step 7., above, is allowed to swirl undisturbed for one hour, at room temperature.

9. Into 15 ml 1/100 M phosphate buffer, pH 6.0, is added:
 a. five milliliters spectral quality methanol
 b. 5/100 ml diaminopropane
 c. 2/100 ml dibromethane, and
 d. 5/100 ml concentrated hydrochloric acid.

10. The crosslinking mixture prepared in step 9., above, is added to the mixture of step 8., above, in equal volume aliquots over a half hour period.

11. The resulting mixture from step 10., above, is then allowed to react for 12 to 16 hours, at room temperature.

12. The final product is washed, and stored as in steps 12 and 13, of Example 19.B.

13. The activity of this preparation is measured as 8.0 Units of glucoamylase per milliliter alumina-glucoamylase composite, in a 1/100 M maltose substrate solution, buffered to 1/100 M in accetate buffer, pH 5.5.

B. Preparation of Immobilized Crude Glucoamylase

1. Thirty grams, −70+80 mesh, porous alumina is weighed out, and washed under distilled, deionized water until the supernatant is clear.

2. This wash is followed by a rinse under one liter of one normal hydrochloric acid.

3. The washed alumina is then placed under 250 ml of 9 normal hydrochloric acid for 1½ hours.

4. The material of step 3., above, is then rewashed as in step 2., above.

5. The alumina is then placed under 250 ml 1/10 M hydrochloric acid, and deaerated for one hour.

6. The alumina is then washed under one liter 1/100 M acetate buffer, pH 5.5, and placed under 100 ml of the same buffer, and allowed to swirl on the laboratory shaker, undisturbed for one half hour, at 0° to 4° C.

7. The enzyme solution is prepared by,
   a. dissolving 6 grams crude glucoamylase (Sigma Chemical Company, Aspergillus Oryzae) into 100 ml 1/100 M phosphate buffer, pH 6.0, over a half hour period to ensure that a good suspension is made.
   b. This material is then centrifuged at 1,375 gravities for a half hour.
   c. the resulting supernatant is decanted off, and saved. The resulting insoluble precipitate is discarded.
   d. The supernatant is filtered through a 2/10 micron pore uncoated filter (Millipore Corporation), with a hand-pump filter unit (Antilia$^{TM}$ Hand Pump) and
   e. ten milliliters of this filtered glucoamylase is retained for insolubilization.

8. The material from step 7 e., above, is added to the mixture prepared in step 6., above.

9. The procedure is the same as for step 8., to step 12., inclusive of the procedure described in Part A. of this section.

10. The activity of this preparation is measured as 9.0 Units of glucoamylase per milliliter of alumina-glucoamylase composite, in a one-hundredth molar maltose substrate solution, buffered to one-hundredth molar acetate buffer, pH 5.5.

EXAMPLE 21

PREPARATION OF THE HYDROGEN PEROXIDE GENERATING REAGENT

1. Thirty grams −60+70 meshed, resieved through an eighty mesh wire screen for five minutes, porous alumina is carefully weighed out, and washed under one liter distilled, deionized water.

2. The alumina is placed under 200 ml of six normal hydrochloric acid for one hour, while swirling, undisturbed for one hour.

3. Glucose oxidase is prepared as in step 7. of Example 19 B, except that Sigma Chemical Company, Type II glucose oxidase was the starting material for purification.

4. Ten milligrams of succinic anhydridde is dissolved in 1 ml of acetone.

5. Three-tenths milliliter of the solution prepared in step 4., above, is added to the enzyme solution of step 3., above, every 10 minutes, and allowed to react undisturbed for 20 minutes after all the solution of step 4., above has been completely added.

6. The material of step 2., above, is then washed under distilled deionized water, until the supernatant is clear.

7. The alumina is then placed under 200 ml distilled, deionized water and deaerated for at least one hour. The supernatant solution is then discarded.

8. The solution of step 5., above, is then added to the alumina of step 7., above, and the pH is adjusted to 4.2.

9. One-tenth gram EDC, i.e., 1-ethyl-3-(3-dimethylaminopropyl) carbodiimide hydrochloride is added to step 8., above. After a half hour reaction period, the pH is adjusted to 5.0, with sodium hydroxide.

10. Four-tenths of a gram of EDC, is dissolved in 30 ml distilled deionized water, and added to step 8., above, at a rate of 1/10 ml per minute.

11. The solution of step 10., above, is allowed to react for 12 to 16 hours, on the laboratory shaker, undisturbed at 0° to 5° C.

12. The final product is washed and stored as in Example 19, Part A, Preparation of the Two-Stage Scavenger Reagent.

13. The activity of this preparation is measured as 24.00 Units glucose oxidase per milliliter aluminaglucose oxidase composite, in a 1/100 molar acetate buffer-substrate solution, pH 5.5, with no detectable amounts of catalase activity.

EXAMPLE 22

SPLIT-STREAM ALPHA-AMYLASE DETERMINATION

An aqueous solution sample of α-amylase is injected with a twenty microliter syringe (Unimetrics) into a flowing buffer stream that is 5/100 molar phosphate, pH 7.2, containing 5/100 molar potassium chloride, and 5/1,000 percent Bio-Ban, and $5 \times 10^{-6}$ M calcium chloride.

The α-amylase solution then flows into an insolubilized glucose polysaccharide substrate (see Example 18) reagent, and by reacting with that substrate releases oligosaccharides, of length, typically, 2 to 6 monomers of glucose. Then, the α-amylase solution flows into a scavenger stage (see Example 19) composed of an immobilized glucose oxidase reagent, followed by an immobilized catalase reagent

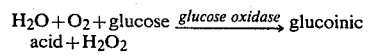

$H_2O + O_2 + \text{glucose} \xrightarrow{\text{glucose oxidase}} \text{glucoinic acid} + H_2O_2$

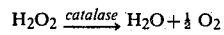

$H_2O_2 \xrightarrow{\text{catalase}} H_2O + \frac{1}{2} O_2$

The now glucose free alpha-amylase sample solution then flows into a mixer, where the stream is mixed almost one-to-one with a second flowing buffer stream composed of one-tenth molar acetate, pH 3.6, 1/10 molar in potassium chloride, and 1/100 percent BIO-BAN. The resulting eluant is then 0.05 M acetate, 0.025 M PO$_4$, 0.0075% BIO-BAN, $2.5 \times 10^{-6}$M CaCl$_2$, and 0.075 M KCl; pH approximately 5.5–5.7.

The oligosaccharides generated by the action of alpha-almylase on immobilized starch, freed of sample glucose in the scavenger stage, is then converted, almost completely by glucose-amylase (see Example 20) to glucose:

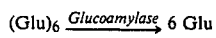

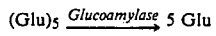

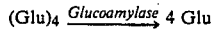

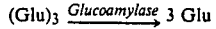

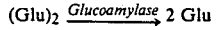

However, this process need not be complete, since the amount of glucose generated will be related to the amunt of α-amylase present in the sample.

The now converted oligosaccharides, in the form of glucose in solution, then flow into the hydrogen peroxide generating stage (see Example 21,) composed of highly purified glucose oxidase, where the glucose generated in the previous stage being a quantitative indicator of the amount of alpha-amylase present in the sample, is converted to a much easier species for detection, i.e., hydrogen peroxide.

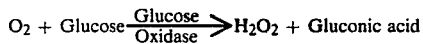

The generated hydrogen peroxide is detected by a flowthrough amperometric sensor, in which a membrane (Spectropore, MW exclusion limit 12-14,000 grams per mole), has been placed between the sensor and the flowing stream. This is done to exclude by diffusion limits and molecular size, most of the substances that the detector is sensitive to, such as ascorbic acid, and uric acid.

A number of samples containing α-amylase were prepared and passed through the above split-stream analytical determination set forth above. The samples were prepared by taking the commerical hog pancreas α-amylase, (Sigma Chemical Company, Type I-A, a suspension of crystalline hog pancreas α-amylase in 0.5 saturated NaCl containing 0.003 molar $CaCl_2$) and diluting the suspension to obtain the concentration set forth in Table II. The samples were individually passed through the split-stream procedure and readings were obtained in an amperometric cell. Each sample was passed through several times and an average signal reading in millivolts was obtained. The results are set forth in Table II and indicate that there is a linear relationship.

TABLE II

| Sample No. | Millivolt Reading | mg % α-amylase |
|---|---|---|
| 1 | 4.70 | 0.212 |
| 2 | 8.00 | 0.808 |
| 3 | 17.50 | 1.00 |
| 4. | 70.00 | 7.42 |
| 5. | 50.00 | 11.5 |

The following Table III sets forth the activities of the immobilized enzymes in the above Examples. Table IV sets forth the amount of starch bound per milliliter of composite in the insoluble substrate stages of Examples 17 and 22.

TABLE III
ACTIVITIES OF IMMOBILIZED REAGENTS

| Reagent | Activity* (U/ml Composite) | Enzyme |
|---|---|---|
| Example 13 | 69.0 | Glucose oxidase |
| Example 13 | 59.0 | Catalase |
| Example 15 | 8.0 | Glucoamylase |
| Example 15 | 8.0 | Alpha-Amylase |
| Example 15 | 10.0 | Maltase |
| Example 16 | 90.0 | Glucose oxidase |
| Example 16 | 4.0 | Catalase |
| Example 19 | 57.0 | Glucose oxidase |
| Example 19 | 18.0 | Catalase |
| Example 19 | 58.5 | Catalase |
| Example 20 | 9.0 | Glucoamylase |
| Example 21 | 24.0 | Glucose oxidase |
| Example 21 | 0.0 | Catalase |

*Rounded off to nearest whole integer

TABLE IV
INSOLUBLE SUBSTRATE

| Reagent | Gm Starch Bound/ml Composite |
|---|---|
| Example 14 | 0.112 |
| Example 18 | 0.105 |

With respect to temperature in the method of determining α-amylase as described above, the procedure can be carried out at temperature ranges between about 5° C. and about 70° C., and the temperature is not considered critical in the procedure. With respect to pH, it should be particularly controlled at the immobilized substrate stage as set forth above in the Examples.

What is claimed is:

1. A method for the quantitative determination of the pancreatic and salivary α-amylases in an aqueous solution sample containing glucose as a contaminant comprising the steps of passing said sample through a scavenger stage containing immobilized scavenger reagents capable of reacting with and removing said glucose as a sample contaminant in the said determination, passing said glucose-free sample through a substrate stage comprising an immobilized starch reagent capable of reacting quantitatively with said α-amylases to produce oligosaccharides, passing said oligosaccharides-containing sample through a glucose-generating stage comprising an immobilized glucose-generating reagent capable of reacting said oligosaccharides to a glucose reaction product, passing said glucose reaction product containing sample to a detection stage comprising an immobilized reagent capable of reacting with said glucose reaction product to generate hydrogen peroxide, determining the amount of said hydrogen peroxide generated in detection means, and relating the detection reading from said detection means to the quantitative amount of α-amylases contained in said sample.

2. The method of claim 1, wherein said aqueous solution sample is diluted with an aqueous buffered diluent.

3. The method of claim 1, wherein said scavenger reagents comprise coimmobilized glucose oxidase and catalase.

4. The method of claim 1, wherein said scavenger stage comprises an immobilized catalase reagent subsequent to said scavenger reagents.

5. The method of claim 1, wherein said immobilized starch reagent is a starch high in amylose content.

6. The method of claim 1, wherein said starch reagent is potato starch.

7. The method of claim 1, wherein said glucose-generating reagent is glucoamylase.

8. The method of claim 1, wherein said glucose-generating reagent is maltase.

9. The method of claim 1, werein said oligosaccharides contain 2-6 monomers of glucose.

10. The method of claim 1, wherein said glucose reaction product in said detection stage is reacted with immobilized glucose oxidase.

11. The method of claim 1, wherein said detection stage comprises polarographic cell means.

12. The method of claim 1, wherein said detection stage comprises spectrographic means.

13. The method of claim 1, wherein said scavenger reagents comprise coimmobilized glucose oxidase and catalase on a hard inorganic porous support.

14. The method of claim 13, werein said porous support is glass.

15. The method of claim 1, wherein said substrate stage comprises an immobilized amylose starch on a porous refractory support.

16. The method of claim 15, wherein said porous support is alumina.

17. The method of claim 1, wherein said substrate stage comprises an amylose starch immobilized and cross-linked on porous alumina.

18. The method of claim 17, wherein said alumina is acid activated.

19. The method of claim 1, wherein said aqueous sample is buffered with an aqueous buffered diluent to pH in the range of about 5 to 7.

20. The method of claim 1, wherein said sample containing said glucose reaction product in said detection stage is passed in direct contact with detection means comprising polarographic electrodes and polarographically determining hydrogen peroxide in said reaction mixture while in direct contact with said electrodes.

21. The method of claim 1, wherein said sample is blood serum.

22. The method of claim 1, wherein said sample is urine.

23. A method for the quantitative determination of the pancreatic and salivary α-amylases contained in a sample of a body fluid wherein said fluid initially contains glucose as a contaminant in the quantitative determination comprising the steps of buffering said sample to a suitable pH value, passing said buffered sample through a scavenger stage containing coimmobilized reagents comprising glucose oxidase and catalase wherein said glucose is removed as a contaminant, passing said glucose-free sample through a substrate stage containing an immobilized starch reagent comprising a high amylose content on an alumina support wherein said starch reagent quantitatively reacts with the α-amylases contained in said sample to produce oliqosaccharides, passing said oligosaccharides-containing sample through a glucose-generating stage containing an immobilized reagent comprising glucoamylase to product a glucose reaction product, passing said glucose-containing sample to a detection stage comprising an immobilized glucose oxidase reagent wherein said glucose reaction product is oxidized to generate hydrogen peroxide, determining with detection means the hydrogen peroxide generated and relating the amount of hydrogen peroxide generated to the quantitative amount of α-amylases contained in said sample.

24. The method of claim 23, wherein said immobilized starch reagent is potato starch cross-linked on said alumina support.

25. The method of claim 23, wherein said sample is passed through said immobilized reagents of said several stages sequentially in a confined zone.

26. The method of claim 23, wherein said detection means comprises polarographic means.

27. The method of claim 23, wherein said detection means comprises spectrographic means.

28. A method for the quantitative determination of the pancreatic and salivary α-amylases contained in an aqueous solution sample containing glucose as a contaminant in the quantitative determination comprising the steps of buffering said sample to a suitable pH value, passing said buffered sample solution through a substrate stage containing an immobilized starch reagent comprising a high amylose content wherein said starch reagent quantitatively reacts with the α-amylases contained in said sample to produce oligosaccharides, passing said oligosaccharides containing sample solution through a scavenger stage containing immobilized reagents wherein said glucose contaminant is removed, mixing said glucose-free, oligosaccharide-containing sample solution with a second buffer solution and passing said buffered sample solution through glucose-generating stage containing immobilized reagents, wherein said reagents produce a glucose reaction product from said oligosaccharides, passing said glucose-containing sample solution to a detection stage werein said glucose reaction product is reacted to generate hydrogen peroxide, passing said hydrogen peroxide containing sample solution through detection means and relating the amount of hydrogen peroxide generated to the quantitative amount of α-amylases in said sample.

29. The method of claim 28, wherein said immobilized starch reagent is potato starch cross-linked on a porous support.

30. The method of claim 28, wherein said sample solution is passed through said scavenger reagents in several stages sequentially in a confined zone.

31. The method of claim 28, wherein said detection means comprises polarographic means.

32. The method of claim 28, wherein said detection means comprises sepctrographic means.

33. The method of claim 28, wherein said scavenger reagents comprise glucose oxidase and catalase.

34. The method of claim 28, wherein said glucose-generating reagent is glucoamylase.

35. The method of claim 28, wherein said glucose-generating reagent is maltase.

36. The method of claim 28, wherein said glucose reaction product is reacted with glucose oxidase.

37. The method of claim 28, wherein said substrate starch reagent is an amylose starch on alumina.

38. The method of claim 28, wherein said substrate starch reagent is an amylose starch immobilized and cross-linked on porous acid-activated alumina.

39. The method of claim 1, wherein said glucose-generating stage comprises immobilized α-amylase.

40. The method of claim 23, wherein said glucose-generating stage comprises immobilized α-amylase.

41. The method of claim 28, wherein said glucose-generating stage comprises immobilized α-amylase.

* * * * *